United States Patent
Temple, Jr.

[11] Patent Number: 5,095,017
[45] Date of Patent: Mar. 10, 1992

[54] 1,2-DIHYDROPYRIDO(3,4,-B)PYRAZINES AS FUNGICIDES

[75] Inventor: Carroll G. Temple, Jr., Birmingham, Ala.

[73] Assignee: Southern Research Institute, Birmingham, Ala.

[21] Appl. No.: 704,217

[22] Filed: May 22, 1991

[51] Int. Cl.$^5$ .................. C07D 471/04; A01N 47/22; A01N 43/90
[52] U.S. Cl. ................................. 514/249; 544/350; 546/308; 552/10; 564/265; 564/364; 568/337
[58] Field of Search .................. 544/350; 514/249

[56] References Cited

U.S. PATENT DOCUMENTS 4,450,160  5/1984  Temple et al. ................ 544/350

Primary Examiner—Mark L. Berch

[57] ABSTRACT

1,2-dihydropyrido[3,4-b]pyrazines are provided which possess antimitotic activity. The compounds have the structure:

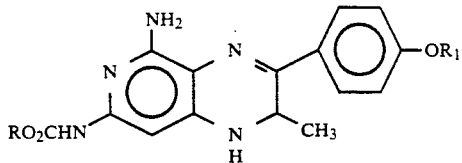

wherein R is a lower alkyl group and $OR_1$ is a member selected from the group consisting of aryl-alkyl ethers having from seven to about 20 carbon atoms, alkyl carbamates having from one to about 12 carbon atoms, the alkyl portion of which may be substituted with a halogen atom, e.g., chlorine, fluorine, bromine or iodine; aryl-alkyl carbamates having from about seven to about 20 carbon atoms, aryl carbamates having from about six to about 20 carbon atoms, aryl-alkyl esters having from about 7 to about 20 carbon atoms, aryl esters having from about six to about 20 carbon atoms, alkylthiocarbamates having from about one to about 12 carbon atoms, aryl-alkylthiocarbamates having from about seven to about 20 carbon atoms, and arylthiocarbamates having from about six to about 20 carbon atoms.

7 Claims, No Drawings

1,2-DIHYDROPYRIDO(3,4,-B)PYRAZINES AS FUNGICIDES

BACKGROUND OF THE INVENTION

This invention relates to novel 1,2-dihydropyrido[3,4-b]pyrazines, also known as 1-deaza-7,8-dihydropteridines.

The antimitotic chemical agents commonly known as spindle poisons are plant products of which the best known are colchicine, podophyllotoxin, and the vinca alkaloids. [L. Wilson, J. R. Bamburg, S. B. Mizel, L. M. Grisham and K. M. Creswell, *Federation Proceedings*, 33, 158 (1974)]. Two members of the latter, vincristine and vinblastine, are currently used clinically in the treatment of neoplasms. Although these agents produce a number of biochemical actions such as the inhibition of macromolecular synthesis, their primary effect is to prevent mitosis by interfering with the function of microtubules, which results in the accumulation of cells in metaphase. In addition, several benzimidazol-2-ylcarbamates have been introduced as fungicides, anthelmintics and antitumoral agents. [L. C. Davidse and W. Flach, *J. Cell Biol.*, 72, 174 (1977). These compounds also prevent mitosis and their biological activity can probably be attributed to interference with the formation or functioning of microtubules.

U.S Pat. No. 4,450,160 to Temple et al discloses that certain 1,2-dihydropyrido[3,4-b]pyrazines possess antifungal and anticancer activity. The compounds have the structure:

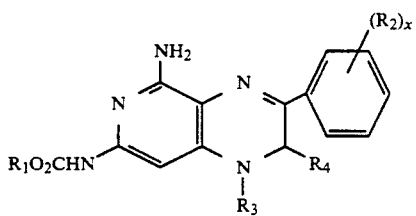

wherein x has a value of 1, 2 or 3; $R_1$ is a lower alkyl group, e.g., an alkyl group containing up to six carbon atoms such as methyl, ethyl, propyl, butyl, etc.; $R_2$ is a member selected from the group consisting of hydrogen, alkyl radicals having from about one to about 12 carbon atoms, preferably from about one to about 6 carbon atoms; alkenyl radicals having from about two to about 15 carbon atoms, preferably from about two to about 10 carbon atoms; cycloalkyl radicals having from about three to about 20 carbon atoms, preferably from about three to about 15 carbon atoms; aralkyl and alkaryl radicals having from about six to about 20 carbon atoms, preferably from about six to about 15 carbon atoms; a halogen radical, e.g., chlorine, fluorine, bromine and iodine, provided that when x has a value o 1 and $R_2$ is in the para position and $R_3$ and $R_4$ are both hydrogen, $R_2$ is not chlorine; a hydroxyl group; an amino group; an alkoxy or aryloxy group; a carboxyl group or an alkylcarboxyl group having from about one to about 10 carbon atoms, preferably from about one to about 5 carbon atoms; an alkylthio group or an arylthio group having from about one to about 20 carbon atoms, preferably from about one to about 15 carbon atoms; a sulfonic acid group or alkyl- or arylsulfonyl group having from about one to about 20 carbon atoms, preferably from about one to about 15 carbon atoms; an alkyl- or arylsulfinyl group having from about one to about 20 carbon atoms, preferably from about one to about 15 carbon atoms; an alkyl- or aryl mono- or diamino group having from about one to about 20 carbon atoms, preferably from about one to about 15 carbon atoms; a hydrocarbyl group, such as defined above, carrying halogen, hydroxyl, amino, alkoxy or aryloxy, and when taken together with the aromatic ring to which it is attached, a fused ring structure such as naphthyl; and $R_3$ and $R_4$ are either both hydrogen or one is hydrogen and the other is a lower alkyl group. The disclosure of this patent is incorporated herein by reference.

SUMMARY OF THE INVENTION

It has now been found that certain 1,2-dihydropyrido[3,4-b]pyrazines which are not disclosed by U.S. Pat. No. 4,450,160 have good antimitotic activity. The compounds of this invention have the structure:

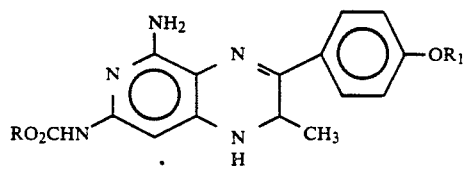

wherein R is a lower alkyl group, e.g., an alkyl group containing up to six carbon atoms such as methyl, ethyl, isopropyl, etc.; and $OR_1$ is a member selected from the group consisting of aryl-alkyl ethers having from seven to about 20 carbon atoms, preferably from about seven to about 15 carbon atoms; alkyl carbamates having from one to about 12 carbon atoms, preferably from about one to about six carbon atoms, the alkyl portion of which may be substituted with a halogen atom, e.g., chlorine, fluorine, bromine or iodine; aryl-alkyl carbamates having from about seven to about 20 carbon atoms, preferably from about seven to about 15 carbon atoms; aryl carbamates having from about six to about 20 carbon atoms, preferably from about six to about 15 carbon atoms; aryl-alkyl esters having from about 7 to about 20 carbon atoms, preferably from about 7 to about 15 carbon atoms; aryl esters having from about six to about 20 carbon atoms, preferably from about six to about 15 carbon atoms; alkylthiocarbamates having from about one to about 12 carbon atoms, preferably from about one to about six carbon atoms; aryl-alkylthiocarbamates having from about seven to about 20 carbon atoms, preferably from about one to about 15 carbon atoms; and arylthiocarbamates having from about six to about 20 carbon atoms, preferably from about six to about 15 carbon atoms.

DETAILED DESCRIPTION OF THE INVENTION

The compounds of this invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of this invention.

Also embraced within the purview of the present invention are therapeutic compositions of matter useful for ameliorating cancer diseases in mammals and containing the 1-deaza-7,8-dihydropteridines of this invention or pharmaceutically acceptable salts thereof.

The active ingredients of the therapeutic compositions and the novel compounds of the present invention inhibit transplanted mouse tumor growth when administered in amounts ranging from about 0.1 mg to about 200 mg per kilogram of body weight per day. A preferred dosage regimen for optimum results would be from about 0.1 mg to about 50 mg per kilogram of body weight per day, and such dosage units are employed that a total from about 7 mg to about 3.5 grams of the active compounds for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatine capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about two and about 60% of the weight of the unit. The amount of active compound in such therapeutically useful compositions is such that a suitable dosage will be obtained. Preferred compositions or preparations according to the present invention are prepared so that an oral dosage unit form contains between about five and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

The following examples illustrate the practice of this invention. In these examples, DMSO is dimethylsulfoxide, MeOH is methyl alcohol, Et$_2$O is diethyl ether, EtOH is ethyl alcohol, MeCN is acetonitrile, and EtOAc is ethyl acetate. In these examples, the underlined numbers refer to the compounds shown in the formulae on pages 10 and 11, in which Et is ethyl.

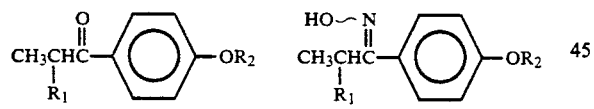

1  $R_1 = Br, R_2 = H$
2  $R_1 = N_3, R_2 = H$
3  $R_1 = N_3, R_2 = H$
4  $R_1 = H_2N, R_2 = H$

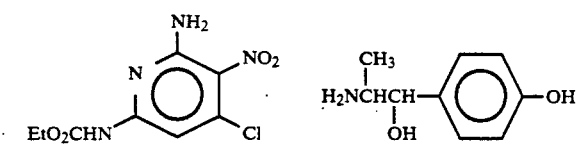

5

6 (1R,2S.tartrate)
7 (1S,2R.tartrate)

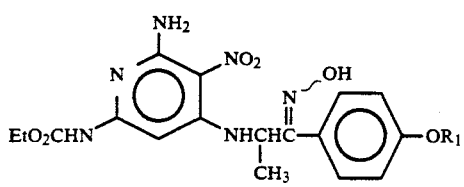

8  $R_1 = H$ (RS)

-continued

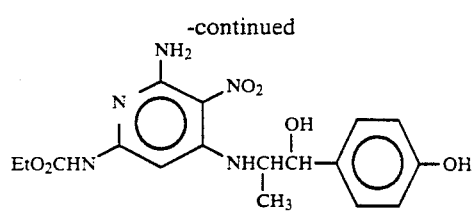

9  (1S,2R)
10 (1R,2S)

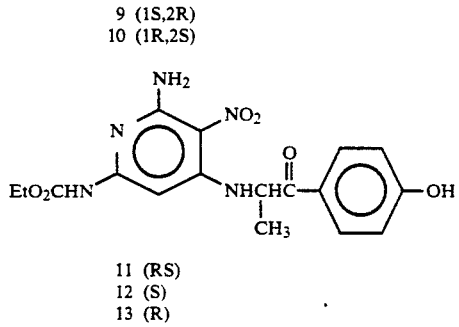

11 (RS)
12 (S)
13 (R)

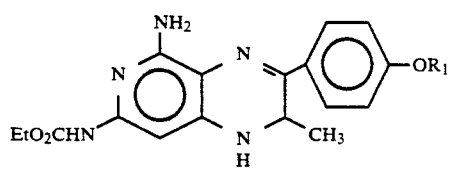

14  $R_1 = H$ (RS)
15  $R_1 = H$ (S)
16  $R_1 = H$ (R)

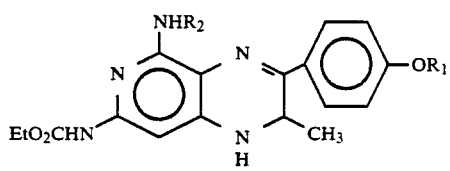

17  $R_1 = C_8H_5CH_2, R_2 = H$
18  $R_1 = BuNHCO, R_2 = H$
19  $R_1 = ClCH_2CH_2NHCO, R_2 = H$ (S)
20  $R_1 = R_2 = ClCH_2CH_2NHCO$ (S)

EXPERIMENTAL SECTION

Example 1

α-Amino-4′-hydroxypropiophenone oxime (4). A solution of sodium azide (398 mg, 6.12 mmol) in deoxygenated (N$_2$) H$_2$O (2 mL) was added to a stirred solution of 1, prepared as described by Dombrovshii et al in Preparation of α-Bromoethyl Aryl Ketones by Bromination of Ethyl Aryl Ketones by Dioxane Dibromide. *J. Gen. Chem.*, U.S.S.R. (Eng. Transl.), 1962, 32, 2246 (1.23 g, 5.37 mmol), in deoxygenated (N$_2$) MeOH (20 mL), and the resulting solution was stirred at room temperature for 16 hours. After removal of MeOH at reduced pressure, the mixture was diluted with water (75 mL) and extracted with Et$_2$O (2×100 mL). The combined organic layers were dried (Na$_2$SO$_4$) and evaporated to give an oil, which solidified on drying in vacuo (P$_2$O$_5$). The off-white solid was triturated with water (100 mL), collected by filtration and dried in vacuo (P$_2$O$_5$) to afford 2: yield, 640 mg.

A solution of 2 (505 mg, 2.64 mmol), hydroxylamine hydrochloride (385 mg, 5.54 mmol) and pyridine (2.5 mL, 31 mmol) in EtOH (10 mL) was heated at reflux for 6 hours and concentrated under high vacuum to give an oil. This residue was extracted with Et$_2$O (3×100 mL), and the combined extracts were evaporated at reduced pressure to afford 3 as a colorless oil: yield, 438 mg.

A solution of crude 3 (5.38 g) from another preparation in EtOH (260 mL) was hydrogenated at atmospheric pressure in the presence of Raney Nickel (6.0 g, weighed wet, washed 3×H$_2$O and 3×EtOH). At 1 hour intervals, the system was evacuated and recharged with fresh hydrogen. After 5 hours, the catalyst was removed by filtration (Celite), the amber-orange filtrate was evaporated at reduced pressure, and the resulting pale-pink solid was dried in vacuo (P$_2$O$_5$) to give 4: yield, 4.3 g. The crude material was used without further purification.

Example 2

4-Hydroxynorephedrine tartrates (6 and 7). A mixture of racemic 4-hydroxynorephedrine (19.0 g, 114 mmol) and D(−)tartaric acid (17.5 g, 117 mmol) in H$_2$O (14 mL) was prepared as described by Smith et al in Agonist Effects of β-Phenethylamines on the Noradrenergic Cyclic Adenosine 3', 5'-Monophosphate Generating System in Rat Limbic Forebrain, J. Med Chem., 1977, 20, 978. The salt was collected by filtration, washed with 2-propanol (150 mL) and Et$_2$O, and recrystallized four times from 2-propanol-H$_2$O (10:1) to give 14.D-tartrate: yield, 13.2 g (73%). A small portion of this salt was dissolved in H$_2$O, treated with an equivalent amount of 1N NaOH, and evaporated to dryness in vacuo. This residue was extracted with hot EtOAc, the extract was evaporated to dryness, and the free base of 6 was reacted with (R)-(−)-1-(1-naphthyl)ethyl isocyanate (98%) in MeCN at 50° C. for 0.5 hour. HPLC chromatograms [5μ Spherisorb OSD1 column, isocratic with 0.02M NH$_4$H$_2$PO$_4$-MeCN (65:35)] on the reaction solution indicated the presence of 6 and 7 in about a 95:5 ratio.

Similarly, the salt from racemic 4-hydroxynorephedrine (17.6 g, 105 mmol) and L(+)-tartaric acid (16.6 g, 111 mmol) was recrystallized five times from 2-propanol-H$_2$O (10:1) to give 7.L-tartrate: yield 9.0 g (54%). Reaction of the free base with (R)-(−)-1-(1-naphthyl)ethyl isocyanate (98%) and determination of the HPLC chromatograms of the reaction solution as described above indicated the presence of 7 and 6 in a 99:1 ratio.

Typical Procedure for the Preparation of
4-[(2-Oxoethyl)amino]pyridine Oximes

Example 3

Ethyl 6-amino-4-[[2-(4-hydroxyphenyl)-1-methyl-2-oxoethyl]amino]-5-nitropyridin-2-ylcarbamate oxime (8) was prepared by refluxing crude 4 (3.96 g), 5 (5.79 g, 22.2 mmol), and triethylamine (3.07 mL, 2.23 g, 22.2 mmol) in 2-propanol (130 mL) for 6 hours. Recrystallization from EtOAc afforded 8: yield 1.49 g.

A second crop (3.85 g, 43%) of slightly impure 8 was obtained by evaporation of the ethyl acetate filtrate and trituration of the residue with Et$_2$O (150 mL).

General Procedure for the Preparation of
4-[(2-Hydroxyethyl)amino]Pyridines

Example 4

Ethyl [S-(R*,S*)]-6-amino-4-[[[2-hydroxy-2-(4-hydroxyphenyl)-1-methyl]ethyl]amino]-5-nitropyridin-2-ylcarbamate (9). A hot solution of 6.D-tartrate (1.02 g, 3.05 mmol, contaminated with 5% of 7.D-tartrate), 5 (0.621 g, 2.38 mmol), and triethylamine (1.18 mL, 0.857 g, 8.48 mmol) in EtOH (10 mL) was refluxed for 21 hours, cooled to room temperature, and added dropwise to H$_2$O (75 mL). The resulting precipitate was collected by filtration, dried in vacuo (P$_2$O$_5$), and purified by flash chromatography (125 g, CHCl$_3$—MeOH, 97:3). The resulting product was triturated with H$_2$O to afford 9 (90% ee) as a yellow glass: yield, 602 mg.

Example 5

Ethyl 6-amino-4-[[[2-(4-hydroxyphenyl)-1-methyl-2-oxo]ethyl]amino]-5nitropyridin-2-ylcarbamate (11). A solution of 8 (3.76 9, 9.30 mmol) in dioxane (80 mL) and 1N HCl (80 mL) was heated at 45° C. for 24 hours. The solution was cooled and adjusted to pH 5 with 1N NaOH. After most of the dioxane was removed at reduced pressure, the mixture was neutralized to pH 7. The clear supernate was decanted from the semisolid residue, which was recrystallized from EtOH (50 mL) to afford 11 as a yellow solid: yield, 2.56 g.

Example 6

Ethyl (S)-6-amino-[[[4-hydroxyphenyl)-2-oxo]ethyl]amino]-5-nitropyridin-2-ylcarbamate (12). Dry pyridine (235 mL) was treated at 0°–5° with CrO$_3$ (7.05 g, 70.5 mmol), and the suspension was stirred for 0.4 hour in the ice bath, after which time a solution of 9 (4.71 g, 12.0 mmol, contaminated with 5% of 10) in dry pyridine (210 mL) was added. The ice bath was removed, stirring was continued 2 hours, and the reaction mixture was poured through a pad of silica gel 60 (100 g). The pad was washed with pyridine (250 mL) and EtOAc (400 mL), and the combined eluate was evaporated to dryness. The resulting semisolid was triturated with water, collected by filtration, and extracted with boiling EtOH (4×250 mL). The combined extracts were evaporated to dryness and the residue was dissolved in EtOAc and poured through a pad of silica gel 60 (50 g, eluted with EtOAc) to remove residual Cr salts: The residue from the evaporation of the eluate was purified by flash chromatography (560 g, CHCl$_3$—MeOH 98:2). The product fractions were combined, evaporated to dryness in vacuo and the resulting residue was triturated with water to afford 12 (90% ee): yield, 1.21 g.

Example 7

Ethyl(S)-5-amino-1,2-dihydro-3-(4-hydroxyphenyl)-2-methylpyrido[3,4-b]pyrazin-7-ylcarbamate (15). A solution of crude 12 (1.05 g, contaminated with 5% of 13) in EtOH (150 mL) was stirred under 1 atm H$_2$ in the presence of Raney Nickel (4 g, weighed wet, washed 3×H$_2$O and 2×EtOH) for 4.5 hours at 60° C. The catalyst was removed by filtration (Celite), the filtrate was evaporated to dryness at reduced pressure and the residue was purified by flash chromatography (120 g, CHCl$_3$—MeOH, 97:3). The product-containing fractions were evaporated to dryness, dissolved in EtOH, filtered, and re-evaporated to afford 15 (90% ee) as a yellow foam: yield, 534 mg.

Example 8

Ethyl 5-amino-1,2-dihydro-3-(4-hydroxyphenyl)-2-methylpyrido[3,4-b]pyrazin-7-ylcarbamate (14) was prepared in the same manner from 11 (0.50 g, 1.3 mmol), but the reaction filtrate was evaporated to dryness at reduced pressure to provide analytically pure 14: yield, 431 mg. HPLC [Enantiopak column, isocratic 95:5

0.05M NaH$_2$PO$_4$ (0.1M NaCl)-2-propanol] indicated a 48:52 mixture of R and S isomers.

Example 9

Ethyl 5-amino-3-[4-(benzyloxy)phenyl]-1,2-dihydro-2-methylpyrido[3,4-b]pyrazin-7-ylcarbamate (17). To a stirred suspension of NaH (13.5 mg of 60% oil-dispersion, washed 1× hexane) in deoxygenated (N$_2$) DMSO was added 14 (101 mg, 0.30 mmol). After stirring 0.2 hour, the nearly-clear amber solution was treated with benzyl chloride (36 mg, 0.29 mmol), stirred 18 hours under N$_2$, and evaporated to dryness. The residue was triturated with de-oxygenated (N$_2$) H$_2$O (10 mL) to give a solid, which was purified by flash chromatography (45 g, CHCl$_3$—MeOH, 99:1) followed by recrystalization from EtOAc-hexane to afford 17 as a pale yellow solid: yield, 44 mg.

Example 10

Ethyl (S)-5-amino-3-[4-[[(2-chloroethylamino)-carbonyloxy]phenyl]-1,2-dihydro-2-methylpyrido[3,4-b]pyrazin-7-ylcarbamate (19) and ethyl (S)-5-[(2-chloroethylamino)carbonylamino]-3-[4[(2-chloroethylamino)-carbonyloxy]phenyl]-1,2-dihydro-2-methylpyrido[3,4-b]pyrazin-7-ylcarbamate (20). To a partial solution of 15.0.3 EtOH.0.5H$_2$O (115 mg, 0.316 mmol, contaminated with 5% of 16) in dry CH$_2$Cl$_2$ (25 mL) under N$_2$ was added 2-chloroethylisocyanate (61 mg, 0.57 mmol), and the suspension was stirred for 20 hours at room temperature under N$_2$. The resulting nearly-clear solution was evaporated to dryness (N$_2$), the residue was dissolved in EtOH (20 mL), stirred for 0.5 hour, and re-evaporated. The residue was purified by column chromatography (55 g, CHCl$_3$—MeOH, 99:1) to afford 20 (90% ee): yield, 52 mg. Further development of the above column (CHCl$_3$—MeOH, 99:1) afforded 19 (90% ee): yield, 56 mg.

Example 11

Ethyl 5-amino-3-[4-[(butylamino)carbonyl-oxy]-phenyl]-1,2-dihydro-2-methylpyrido[3,4-b]pyrazin-7-ylcarbamate (18) was prepared by stirring 14.0.2 EtOH.0.8 H$_2$O (101 mg, 0.277 mmol) and n-butyl isocyanate (41 mg, 41 mmol) in dry CH$_2$Cl$_2$ (25 mL) for 144 hours at room temperature. Workup with EtOH and flash chromatography (20 g, CHCl$_3$—MeOH, 90:2) afforded 18: yield, 24.7 mg.

The properties of the compounds prepared in the foregoing examples are set forth in Table I. The elemental analyses are set forth in Table II. Melting and decomposition temperatures were determined in capillary tubes in a Mel-Temp apparatus. The $^1$H NMR spectra were determined on DMSO-d$_6$ solutions with either a Varian XL-100-15 or a Nicolet NT300NB spectrometer with tetramethylsilane as internal standard. Optical rotations (±2%) were measured with a Perkin-Elmer Model 241 Automatic Polarimeter. Mass spectra were taken with a Varian Mat 311A spectrometer operating in either the electron-impact or fast-atom-bombardment mode to provide the M$^+$ and (M+1)$^+$ molecular ion, respectively. The progress of reactions was followed by thin-layer chromatography (TLC) on plates of silica gel from Analtech, Inc. HPLC chromatograms were determined on an ALC-242 liquid chromatograph equipped with a UV detector (254 nm) and an M-6000 pump. Flash chromatography was performed with silica gel 60 (230-400 mesh) from E. Merck. Raney Nickel No. 2800 was obtained from Davison Speciality Chemical Co. Where analyses are indicated only by symbols of the elements, analytical results obtained for those elements were within 0.4% of the theoretical value.

TABLE I

PROPERTIES OF COMPOUNDS

| Compounds | Yield, % | mp, °C. | $[\alpha]_D^{25}$ deg$^a$ | mass spectra$^b$ | $^1$H NMR spectra$^b$ selected peaks, δ | formula | anal. |
|---|---|---|---|---|---|---|---|
| 2 | 62 | 79-84 | | 192[M + 1]$^+$ | 5.05 q(2-CH) | C$_9$H$_9$N$_3$O$_2$ | C,H,N |
| 3 | 78 | oil | | 206[M]$^+$ | 5.36 q(1'-CH), 4.55 q(1'-CH)$^{d,e}$ | C$_9$H$_{10}$N$_4$O$_2$0.3H$_2$O | C,H,N |
| 4 | −91$^f$ | 143-7 | | 181[M+ 1]$^+$ | 4.30 q(1'-CH), 3.77 q(1'-CH)$^e$ | | |
| 6$^g$ | 73 | 179-82 dec | −34.9 [c,0.8/H$_2$O]$^h$ | | 3.31 m(2'-CH), 4.80 d(1'-CH)$^d$ | C$_{13}$H$_{19}$NO$_8$H$_2$O | C,H,N |
| 7$^i$ | 54 | 183-4 dec | +34.8 [c,1.0/H$_2$O] | | 3.31 m(2'-CH), 4.80 d(1'-CH)$^d$ | C$_{13}$H$_{19}$NO$_8$1.1H$_2$O | C,H,N |
| 8 | 60$^f$ | 173-5 | | 405[M + 1]$^+$ | 5.07 quin (1'-CH), 4.61 quin (1'-CH)$^{e,k}$ | C$_{17}$H$_{20}$N$_6$O$_6$ 0.3 CH$_3$CH$_2$O$_2$CCH$_3$ | C,H,N |
| 9 | 65 | >125 dec | +149 [c,1.2/MeOH] | 392[M + 1]$^+$ | 3.66 m (1'-CH), 4.76 t (2'-CH)$^d$ | C$_{17}$H$_{21}$N$_5$O$_6$0.4H$_2$O | C,H,N |
| 10 | 61 | >125 dec | +154 [c,0.8/MeOH] | 392[M + 1]$^+$ | 3.66 m (1'-CH), 4.76 t (2'-CH)$^d$ | C$_{17}$H$_{21}$N$_5$O$_6$0.5H$_2$O | C,H,N |
| 11 | 71 | 209-11 dec | | 390[M + 1]$^+$ | 5.31 quin (1'-CH) 9.79 d (4-NH)$^j$ | C$_{17}$H$_{19}$N$_5$O$_6$0.2 CH$_3$CH$_2$OH | C,H,N |
| 12 | 26 | 197 dec | +18.0 [c,1.2/dioxane] | 390[M + 1]$^+$ | 5.32 quin (1'-CH) 9.80 d (4-NH)$^d$ | C$_{17}$H$_{19}$N$_5$O$_6$0.5H$_2$O | C,H,N |
| 13 | 22 | 190 dec | −21.4 [c,1.0/dioxane] | 390[M + 1]$^+$ | 5.31 quin (1'-CH) 9.79 d (4-NH)$^{dj}$ | C$_{17}$H$_{19}$N$_5$O$_6$0.3H$_2$O 0.2-CH$_3$CH$_2$OH | C,H,N |
| 14 | 97 | >140 dec | — | 341[M]$^+$ | 4.72 m (2-CH) 6.88 br (1-NH)$^{dj}$ | C$_{17}$H$_{19}$N$_5$O$_3$0.8H$_2$O 0.2-CH$_3$CH$_2$OH | C,H,N |
| 15 | 58 | >135 dec | −538 [c,0.7/MeOH]$^g$ | 341[M]$^+$ | 4.73 m (2-CH), 6.86 br (1-NH)$^{dj}$ | C$_{17}$H$_{19}$N$_5$O$_3$0.5H$_2$O 0.3-CH$_3$CH$_2$OH | C,H,N |
| 16 | 94 | >135 dec | +665 [c,1.0/MeOH]$^l$ | 342[M + 1]$^+$ | 4.72 m (2-CH), 6.84 br (1-NH)$^{dj}$ | C$_{17}$H$_{19}$N$_5$O$_3$0.1H$_2$O 0.4-CH$_3$CH$_2$OH | C,H,N |
| 17 | 34 | >175 dec | — | 432[M + 1]$^+$ | 4.77 m (2-CH), 6.89 d (1-NH)$^o$ | C$_{24}$H$_{25}$N$_5$O$_3$0.25 CH$_3$(CH$_2$)$_4$CH$_3$ | C,H,N |
| 18 | 20 | 130-5 dec | — | 441[M + 1]$^+$ | 4.80 m (2-CH), 6.95 d (1-NH)$^{d,m}$ | C$_{22}$H$_{28}$N$_6$O$_4$0.3 H$_2$O0.1CH$_3$OH | C,H,N |
| 19 | 40 | >220 dec | — | 447[M + 1]$^+$ | 4.80 m (2-CH), 6.96 br (1-NH)$^p$ | C$_{20}$H$_{23}$ClN$_6$O$_4$ 0.3-CHCl$_3$ | C,H,N |
| 20 | 30 | >195 dec | — | 552[M+ 1]$^+$ | 4.94 m (2-CH), | C$_{23}$H$_{27}$Cl$_2$N$_7$O$_5$ | C,H,N$^q$ |

TABLE I-continued

PROPERTIES OF COMPOUNDS

| Compounds | Yield, % | mp. °C. | $[\alpha]_D^{25}$ deg[a] | mass spectra[b] | $^1$H NMR spectra[b] selected peaks. δ | formula | anal. |
| --- | --- | --- | --- | --- | --- | --- | --- |
| | | | | | 7.49 br (1-NH)[p] | 0.2-CHCl$_3$ | |

[a] sample weights were corrected to correspond to anhydrous material.
[b] see Experimental Section.
[c] overall crude yield from 4.
[d] H$_2$O observed, δ 3.32.
[e] see discussion, ratio of oxime isomers (Z:E): 9, 93:7; 10, 5:6; 11, 7:6; 16, 1:3; 17, 1:0 (another crop showed both isomers); 18(A), 0:1; 18(B), 9:1.
[f] crude yield.
[g] 90% ee.
[h] reference 9; $[\alpha]_D^{25}$; −34° [c 1.93/H$_2$O].
[i] 98% ee.
[j] EtOH observed, δ 1.06 t, 3.45 q.
[k] EtOAc observed, δ 1.17 t, 1.99 s, 4.02 q.
[l] overall crude yield.
[m] CH$_3$OH observed, δ 3.17 s.
[n] presoftening from 109° C.
[o] hexane observed, δ 0.86 m, 1.22 m.
[p] CHCl$_3$ observed, δ 8.32 s.
[q] N:calcd. 17.01; found. 16.52.

TABLE II

| | Elemental Analysis | | | | | |
| --- | --- | --- | --- | --- | --- | --- |
| | Calcd. | | | Found | | |
| Compound | C | H | N | C | H | N |
| 2 | 56.54 | 4.74 | 21.98 | 56.66 | 4.85 | 21.77 |
| 3 | 51.08 | 5.05 | 26.48 | 51.23 | 5.37 | 26.47 |
| 6 | 46.57 | 6.31 | 4.18 | 46.58 | 6.30 | 4.17 |
| 7 | 46.32 | 6.34 | 4.15 | 46.46 | 6.48 | 4.18 |
| 8 | 50.74 | 5.24 | 19.51 | 50.62 | 5.18 | 19.37 |
| 9 | 51.23 | 5.51 | 17.57 | 50.96 | 5.81 | 17.71 |
| 10 | 51.00 | 5.54 | 17.49 | 50.89 | 5.42 | 17.71 |
| 11 | 52.43 | 5.11 | 17.57 | 52.42 | 5.07 | 17.54 |
| 12 | 51.26 | 5.06 | 17.58 | 51.01 | 5.12 | 17.70 |
| 13 | 51.73 | 5.19 | 17.34 | 51.66 | 5.23 | 17.39 |
| 14 | 57.26 | 6.02 | 19.19 | 57.19 | 5.85 | 19.07 |
| 15 | 58.04 | 6.03 | 19.23 | 57.95 | 5.84 | 19.23 |
| 16 | 59.13 | 6.02 | 19.37 | 59.06 | 6.10 | 19.56 |
| 17 | 67.61 | 6.34 | 15.46 | 67.68 | 6.66 | 15.45 |
| 18 | 59.10 | 6.51 | 18.71 | 59.28 | 6.63 | 18.40 |
| 19 | 50.51 | 4.87 | 17.41 | 50.88 | 5.07 | 17.18 |
| 20 | 48.35 | 4.76 | 17.01 | 48.62 | 5.11 | 16.52 |

Biological data is shown in Table III.

TABLE III

| | Biological Data | | | |
| --- | --- | --- | --- | --- |
| | L1210[a] | L1210[b] | P388[c], 10$^6$ Tumor Cell Implant, i.p., qd 1-5 | |
| Compound | IC$_{50}$ nM | MI$_{0.5}$ nM | Dose (mg/kg) | % ILS[d] |
| 14 | 0.22 | 0.47 | 0.5 | 55 |
| 15 | 0.18 | 0.30 | 0.22 | 58 |
| 16 | 32[e] | | 25 | 77[e] |
| 17 | 7 | 30 | 1 | 120 |
| 18 | 0.47 | | 0.25 | 120[f] |
| 19 | 0.043 | | 1 | 90 |
| 20 | 570 | — | — | — |

[a] Nanomolar concentration of agent that inhibits proliferation of cultured lymphoid leukemia L1210 cells to 50% control growth during 48 hours.
[b] Nanomolar concentration of agent that causes a mitotic index (number of cells in mitosis divided by total cells) of 0.5 for cultured lymphoid leukemia L1210 cells during an exposure period of 12 hours.
[c] Lymphocytic leukemia P388.
[d] Increase in life span at the highest nontoxic dose tested.
[e] Average of two determinations.
[f] Toxic at a dose of 1 mg/kg; when repeated at the 0.25 mg/kg dose, 1/6 45th day survivor.

In contrast to 14 and 15, the benzyl ether 17 showed a decrease in cytotoxicity and antimitotic activity to cultured cells and gave a greater increase in life span in mice at about the same dose relative to 14 and 15. In addition, relative to 16, 17 was active at a lower dose in vivo. In contrast, the phenyl carbamates 18 and 19 showed similar or greater in vitro activity and the possibility of greater selectivity in vivo relative to 14 and 15. As indicated by the IC$_{50}$ value, substitution on the 5-amino group of 19 to give 20 reduced activity significantly.

What is claimed is:

1. A 1,2-dihydropyrido[3,4-b]pyrazine having the formula:

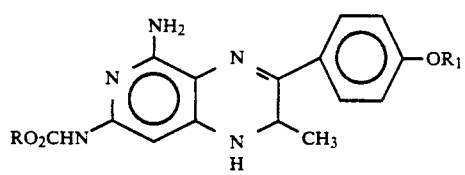

wherein R is a lower alkyl group and OR$_1$ is a member selected from the group consisting of aryl-alkyl ethers having from seven to 15 carbon atoms, alkyl carbamates having from one to 12 carbon atoms, the alkyl portion of which may be substituted with a halogen atom, aryl-alkyl carbamates having from seven to 20 carbon atoms, aryl carbamates having from six to 20 carbon atoms, aryl-alkyl esters having from 7 to 20 carbon atoms, aryl esters having from six to 20 carbon atoms, alkylthiocarbamates having from one to 12 carbon atoms, aryl-alkylthiocarbamates having from seven to 20 carbon atoms, and arylthiocarbamates having from six to 20 carbon atoms.

2. A compound as defined in claim 1, where R is ethyl.

3. A compound as defined in claim 2 wherein R$_1$ is selected from the group consisting of those having the following structures

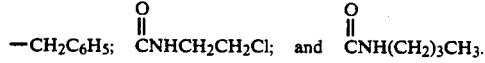

4. A compound as defined in claim 1 wherein R$_1$ is CH$_2$C$_6$H$_5$.

5. A compound as defined in claim 1 wherein R$_1$ is

6. A compound as defined in claim 1 wherein R$_1$ is

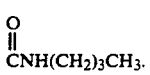

7. A pharmaceutical composition in dosage unit form comprising an amount of a compound as defined by claim 1 effective to treat fungal diseases in association with a pharmaceutical carrier.

* * * * *